United States Patent

Brown, Jr.

[11] Patent Number: 5,185,010
[45] Date of Patent: Feb. 9, 1993

[54] SPIRALLY WOUND TAMPON WITH OVERWRAP

[75] Inventor: Robert W. Brown, Jr., Hampden, Mass.

[73] Assignee: Tambrands Inc., White Plains, N.Y.

[21] Appl. No.: 828,756

[22] Filed: Jan. 31, 1992

[51] Int. Cl.⁵ ............... A61F 13/22; A61F 13/48
[52] U.S. Cl. .................... 604/379; 604/374; 604/385.1; 604/904
[58] Field of Search ........ 604/379, 385.1, 904, 604/366, 370, 374, 380; 156/190, 192

[56] References Cited

U.S. PATENT DOCUMENTS

| | | | |
|---|---|---|---|
| 2,926,667 | 3/1960 | Burger et al. | 604/379 X |
| 3,670,731 | 6/1972 | Harmon | 604/368 |
| 3,732,866 | 5/1973 | Accavallo | 604/379 |
| 4,018,225 | 4/1977 | Elmi | 604/374 X |
| 4,232,674 | 11/1980 | Melican | 604/370 X |
| 4,598,528 | 7/1986 | McFarland et al. | 604/385.1 X |
| 4,642,108 | 2/1987 | Sustmann | 604/379 |
| 4,699,618 | 10/1987 | Sustmann | 604/365 |
| 4,816,100 | 3/1989 | Friese | 156/191 |
| 4,863,450 | 9/1989 | Friese | 604/370 |

FOREIGN PATENT DOCUMENTS 3740208  6/1989  Fed. Rep. of Germany ...... 604/904

Primary Examiner—Randall L. Green
Assistant Examiner—D. Willse
Attorney, Agent, or Firm—Fish & Richardson

[57] ABSTRACT

A tampon is provided which includes an absorbent material (12) wound in a spiral configuration, the outermost winding (18) of the spiral having a liquid permeable overwrap material (10) disposed thereon, a portion of said overwrap being folded over the edge (18) of the spiral which corresponds to the withdrawal end of the tampon and adhered (seal 16) to the inside surface (13) of the outermost winding.

29 Claims, 2 Drawing Sheets

SPIRALLY WOUND TAMPON WITH OVERWRAP

BACKGROUND OF THE INVENTION

The invention relates to a spirally wound overwrapped tampon.

Tampons may be formed by providing a length of absorbent material, e.g. a nonwoven web, spirally winding the material upon itself, and compressing the wound material radially. These spirally wound tampons are often provided with an overwrap, i.e. an outer covering of a liquid permeable material, typically a thermoplastic film, to improve the lubricity of the tampon, reducing insertion and withdrawal forces, and to prevent fibers of the nonwoven from being detached ("fiber fluff-off") during insertion and withdrawal.

An overwrapped, spirally wound tampon is disclosed in U.S. Pat. No. 4,816,100. This tampon has a liquid-permeable, thermoplastic strip section bonded by heat-sealing to the outside of the nonwoven web section over a length which approximately corresponds to the length of the circumference of the wound tampon. The outer end of the strip section, which projects beyond the end of the nonwoven web section, is welded to the outside of part of the strip section sealed to the nonwoven web section. Both the insertion and withdrawal end of the tampon remain free of the overwrap material. The patent indicates that it is necessary to bond the overwrap to the surface of the tampon in order to guarantee that the high absorbency of the nonwoven material, based on capillary action, continues through the overwrap material.

One problem which may occur with overwrapped tampons is peeling back of the overwrap from the surface of the absorbent material when the tampon is removed after use ("peel back"). This may cause discomfort and disturb the user, and may even result in part or all of the overwrap tearing off.

SUMMARY OF THE INVENTION

We have discovered that a tampon having a desired absorbency and excellent resistance to peel back can be formed by a process including the steps of (a) adhering, lengthwise, a length of liquid permeable overwrap material, slightly longer than the circumference of the assembled tampon, to the interior surface of a length of absorbent material (i.e., the surface opposite that which is exposed in the finished tampon), (b) folding the overwrap over one edge of the absorbent material, and (c) rolling the absorbent material, starting at the end which is not overwrapped, so that the overwrap material covers the outside of the finished tampon and the adhered areas are on the inside of the tampon.

In one aspect, the invention relates to a tampon comprising an absorbent material wound in a spiral configuration, the outermost winding of the spiral having a liquid permeable overwrap material disposed thereon, a portion of said overwrap being folded over an edge of the outer layer of the spirally wound material and adhered to the inside surface of said outermost winding.

In preferred embodiments of the invention, the overwrap is folded over the edge corresponding to the withdrawal edge of the finished tampon, the overwrap is slightly greater in length than the outer circumference of the tampon and extends beyond the end of the outermost winding of absorbent material, forming a tab which is sealed to the overwrap; the overwrap material is folded over both edges of the absorbent material; and the overwrap material is adhered, prior to winding, widthwise to the absorbent material, preferably in an area which will be inside the tampon after it is rolled up.

In other preferred embodiments of the invention, the overwrap material is thermoplastic, and is adhered to the absorbent material by heat-sealing, preferably combined with applied pressure; the overwrap covers substantially the entire outer circumferential surface of the tampon; the overwrap is longer than it is wide; the overwrap material which is folded over the edge of the spiral extends about 5 to 20 mm past the edge of the absorbent material on the inner surface of the spiral; the overwrap material is a bicomponent polypropylene/polyethylene nonwoven; the overwrap material has a thickness of from about 0.05 mm to 0.30 mm; the overwrap material has a basis weight of from about 7 g/m$^2$ to 25 g/m$^2$, more preferably about 10 g/m$^2$ to 14 g/m$^2$; the wound tampon is primarily radially compressed; and the absorbent material is selected from the group consisting of cellulosic fibers, cotton fibers, rayon fibers and blends thereof, more preferably blends of cotton and rayon fibers.

In addition to good absorbency and resistance to peel back, the tampon of the invention has a smooth, soft feel, due to the absence of any hard spots on its surface which may result from bonding of the overwrap to the absorbent material.

Other features of the invention will be apparent from the following description of the preferred embodiments, and from the claims.

DESCRIPTION OF THE PREFERRED EMBODIMENTS

A preferred technique for winding and assembling a tampon of the invention is illustrated in FIGS. 1a-1e.

Figure 1A:
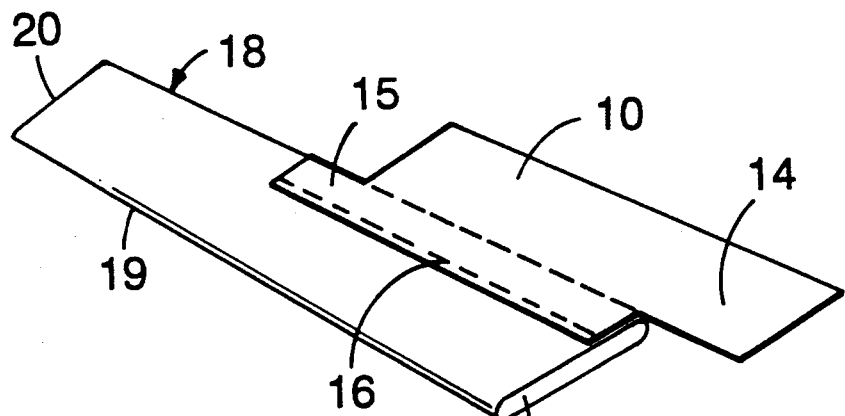
FIGS. 1a-1e are perspective views which show the steps in the winding of a tampon according to one embodiment of the invention.

FIG. 1a shows a length of absorbent material 12, having an inner surface 13, to which overwrap material 10 is adhered, forming seal 16. Overwrap material 10 extends beyond outer end 21 of absorbent material 12, forming a tab 14. To simplify cutting of the overwrap material from a web, the overwrap material extends along the absorbent material in area 15, which corresponds to the cut out area under tab 14. In a preferred embodiment, the overwrap material is cut in a rectangle, and the overwrap is folded over itself in the area of tab 14, forming a double thickness of material in that area.

Figure 1B:
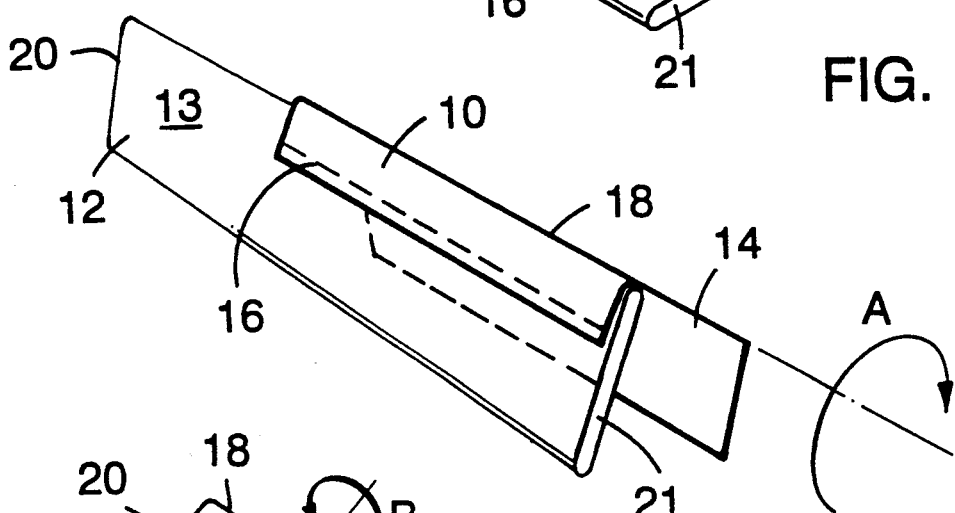

In FIG. 1b, overwrap 10 is folded over edge 18 of absorbent material 12, in the direction indicated by arrow A.

Figure 1C:
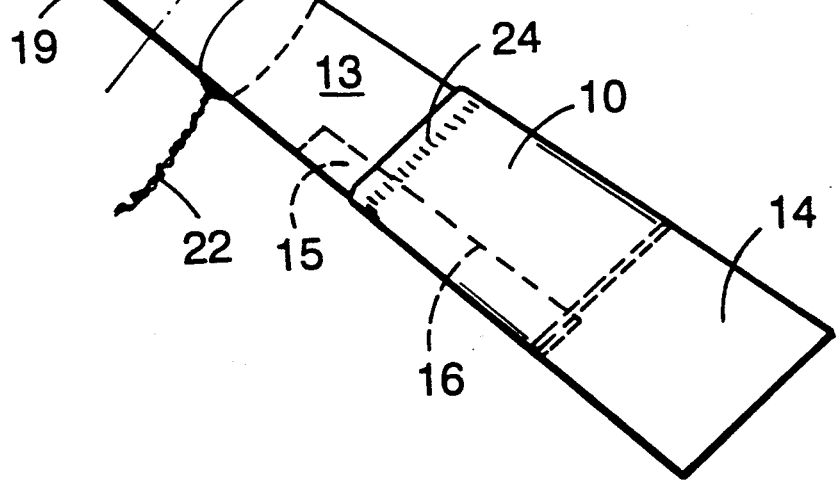

In FIG. 1c, the overwrap/absorbent assembly has been turned over, so that seal 16 is facing in. Widthwise seal 24 is formed, to retain the overwrap in its folded over position. Also, withdrawal cord 22 is looped over an area of the absorbent material near to inner end 20. Spiral winding is then begun, starting at or near end 20, and progressing in the direction indicated by arrow B.

Figure 1D:
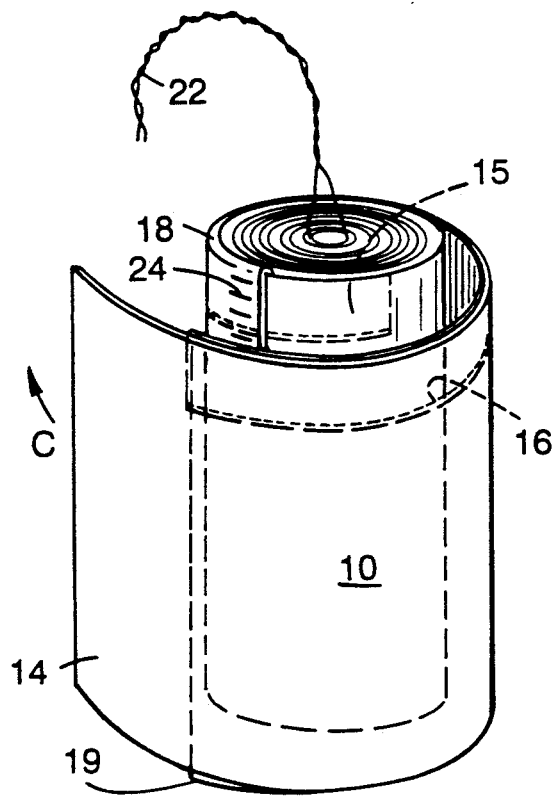
Figure 2:
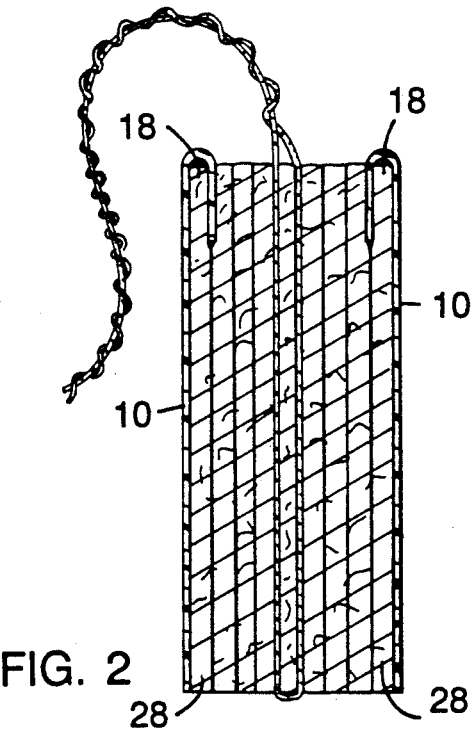
FIG. 2 is a cross-sectional view taken along 2—2 in FIG. 1e.

FIG. 1d shows tampon after all of the absorbent material has been wound into a spiral. The outermost winding of the spiral (reference number 28 in FIG. 2) is entirely covered by overwrap 10, and widthwise seal 24 will be covered either by end 21 of absorbent material 12 (preferably) or by tab 14 of overwrap 10. After the final winding of the absorbent material, tab 14 is wound around the overwrapped surface in the direction indicated by arrow C. In an alternate embodiment, overwrap 10 does not extend all the way to edge 19 of the absorbent material, i.e. less than the entire circumferential surface of the absorbent material is covered.

Figure 1E:
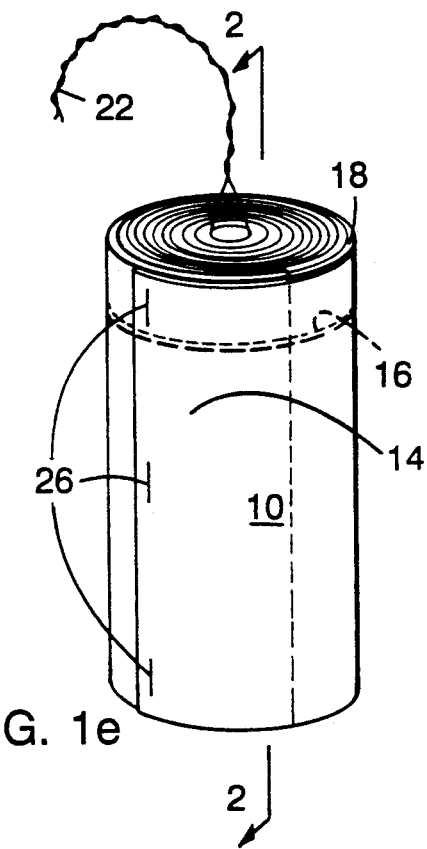

Finally, as shown in FIG. 1e, tab 14 is sealed to the overwrapped surface by tab seal 26. In this embodiment, tab seal 26 is a discontinuous (intermittent) seal, to enhance the softness of the sealed area. In other embodiments, tab seal 26 may be continuous.

Figure 3:
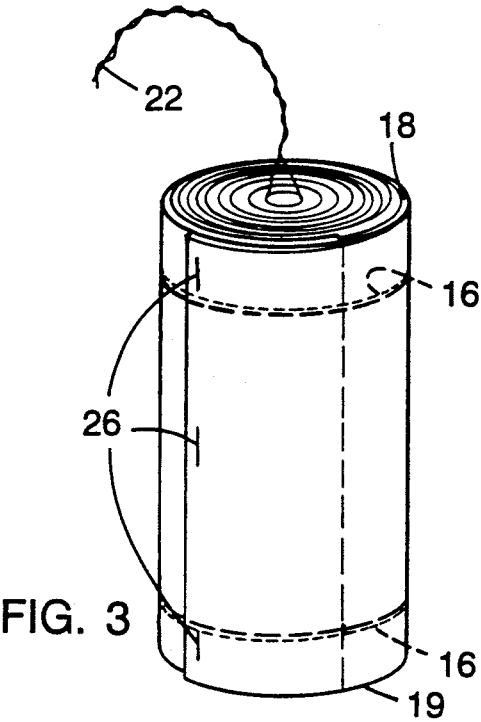
FIG. 3 is a perspective view of another embodiment of the invention.

As shown in FIG. 3, the overwrap material may extend over both edges of the absorbent material (edges 18 and 19 in FIGS. 1a-1c), and be sealed on the inside surface of the absorbent material, using the process shown in FIGS. 1a-1e. In this embodiment of the invention, both the insertion and withdrawal ends of the tampon are smoothed by the folded-over overwrap, and both ends are protected from peel back.

Seals 16, 24 and 26 are preferably all heat seals, and accordingly it is preferred that the overwrap be a heat sealable thermoplastic. It is preferred that the seals be intermittent, particularly the overwrap to overwrap seal (seal 26) which will be exposed in the assembled tampon and is thus is preferably soft. However, continuous seals may be used, and the seals may be either smooth or textured, as desired. Appropriate sealing techniques are known in the art.

Any conventional absorbent material is suitable for use in the invention. It is preferred that the material be one to which the overwrap material selected may be readily heat sealed. Preferred absorbent materials are selected from the group consisting of cellulosic fibers, cotton fibers, rayon fibers and blends thereof. Most preferred are blends of cotton and rayon fibers.

The tampons of the invention may be manufactured using commercially available tampon winding machines made by Karl Ruggli AG, Fisibach, Switzerland.

While preferred embodiments have been described above, other variations and modifications are within the scope of the following claims. For example, instead of a thermoplastic material, other overwrap materials may be used, and that material may be a fabric or a nonwoven; instead of heat sealing, other sealing methods may be utilized, e.g. adhesives, powder bonding or stitching; different processes may be used to obtain the tampon of the invention, other than that which is shown in FIGS. 1a-1e; other machines may be utilized to spirally wind the tampon, e.g. the "Falu" made by K. Fassbind-Ludwig & Co., Fulu Machinenbau, Wagen bei Jona, Switzerland.

I claim:

1. A tampon adapted for insertion into a body cavity, comprising a length of absorbent material wound in a spiral configuration and compressed, the outermost winding of the spiral having a liquid permeable overwrap material disposed thereon, a portion of said overwrap being folded over an edge of the outer layer of the spirally wound material and adhered to the inside surface of said outermost winding.

2. The tampon of claim 1 wherein the overwrap is folded over the edge corresponding to the withdrawal edge of the finished tampon.

3. The tampon of claim 1 wherein the overwrap is slightly greater in length than the outer circumference of the tampon.

4. The tampon of claim 3 wherein the overwrap is disposed on the absorbent material such that it extends beyond the end of the outermost winding of absorbent material, forming a tab which is sealed to the overwrap.

5. The tampon of claim 1 wherein the overwrap material is folded over both edges of the absorbent material.

6. The tampon of claim 1 wherein the overwrap material is adhered widthwise to the absorbent material in an area which will be inside the tampon after it is rolled up.

7. The tampon of claim 1 wherein the overwrap material is thermoplastic.

8. The tampon of claim 7 wherein the overwrap is adhered to the absorbent material by pressure and heat-sealing.

9. The tampon of claim 1 wherein the overwrap covers substantially the entire outer circumferential face of the tampon.

10. The tampon of claim 1 wherein the overwrap is longer than it is wide.

11. The tampon of claim 1 wherein the overwrap material which is folded over the edge of the spiral extends about 5 to 20 mm past the edge of the absorbent material on the inner surface of the spiral.

12. The tampon of claim 1 wherein the overwrap material is a bicomponent polypropylene/polyethylene nonwoven.

13. The tampon of claim 1 wherein the overwrap material has a thickness of from about 0.05 to 0.30 mm.

14. The tampon of claim 1 wherein the wound tampon is substantially only radially compressed.

15. The tampon of claim 1 wherein the absorbent material is selected from the group consisting of cellulosic fibers, cotton fibers, rayon fibers and blends thereof.

16. The tampon of claim 15 wherein the absorbent material is a blend of cotton and rayon fibers.

17. The tampon of claim 1 wherein the overwrap material has a basis weight of from about 7 $g/m^2$ to 25 $g/m^2$ 18. The tampon of claim 17 wherein the overwrap has a basis weight of from about 10 $g/m^2$ to 14 $g/m^2$.

19. A process for manufacturing an overwrapped spirally wound tampon, having a withdrawal end and an insertion end, comprising the steps of:
(a) adhering, lengthwise, a length of liquid permeable overwrap material, slightly longer than the circumference of the assembled tampon, to the interior surface of a length of absorbent material;
(b) folding the overwrap over one edge of the absorbent material;
(c) rolling the absorbent material to form the tampon, starting at the end which is not overwrapped, so that the overwrap material substantially covers the outside of the rolled tampon and the adhered areas are on the inside of the tampon.

20. The process of claim 19 further comprising the step of (d) radially compressing the tampon.

21. The process of claim 19 wherein the overwrap is folded over the edge of the absorbent material which corresponds to the withdrawal end of the tampon.

22. The process of claim 19 wherein, prior to rolling, the overwrap material is adhered widthwise to the absorbent material in an area which will be inside the tampon after it is rolled up.

23. The process of claim 19 wherein the overwrap material is thermoplastic.

24. The process of claim 23 wherein the overwrap is adhered to the absorbent material by heat-sealing.

25. The process of claim 19 wherein the overwrap covers substantially the entire outer circumferential surface of the tampon.

26. The process of claim 19 wherein the overwrap is longer than it is wide.

27. The process of claim 19 wherein the overwrap material which is folded over the edge of the spiral extends about 5 mm to 20 mm past the edge of the absorbent material on the inner surface of the spiral.

28. The process of claim 19 wherein the overwrap is a bicomponent polypropylene/polyethylene nonwoven.

29. The process of claim 19 wherein the overwrap is folded over both edges of the absorbent material.

* * * * *